(12) United States Patent
Yoshii et al.

(10) Patent No.: US 8,575,067 B2
(45) Date of Patent: Nov. 5, 2013

(54) HERBICIDAL COMPOSITION HAVING THE HERBICIDAL EFFECT ENHANCED, AND METHOD FOR ENHANCING THE HERBICIDAL EFFECT

(75) Inventors: Hiroshi Yoshii, Kusatsu (JP); Yoshiaki Ishihara, Kusatsu (JP); Ryu Yamada, Kusatsu (JP); Tatsuhiko Tsuruta, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 1003 days.

(21) Appl. No.: 10/562,980

(22) PCT Filed: Jun. 30, 2004

(86) PCT No.: PCT/JP2004/009598
§ 371 (c)(1),
(2), (4) Date: Dec. 30, 2005

(87) PCT Pub. No.: WO2005/009132
PCT Pub. Date: Feb. 3, 2005

(65) Prior Publication Data
US 2006/0154824 A1   Jul. 13, 2006

(30) Foreign Application Priority Data
Jul. 25, 2003   (JP) .................................. 2003-280259

(51) Int. Cl.
*A01N 47/36* (2006.01)
*A01N 25/22* (2006.01)

(52) U.S. Cl.
USPC ........................................ 504/215; 504/116

(58) Field of Classification Search
USPC ............................ 424/465; 504/215, 367, 116
See application file for complete search history.

(56) References Cited

U.S. PATENT DOCUMENTS

| | | | | |
|---|---|---|---|---|
| 5,411,932 A | * | 5/1995 | Yoshida et al. | 504/132 |
| 5,668,086 A | * | 9/1997 | Tadayuki et al. | 504/235 |
| 5,830,827 A | * | 11/1998 | Maeda | 504/215 |

FOREIGN PATENT DOCUMENTS

| | | |
|---|---|---|
| CN | 1279015 A | 1/2001 |
| EP | 0 313 317 | 4/1989 |
| EP | 0 598 515 | 5/1994 |
| GB | 2 309 904 | 8/1997 |
| RU | 2 054 427 C1 | 2/1996 |
| RU | 2 113 793 C1 | 6/1998 |
| WO | 98/16102 | 4/1998 |
| WO | 00/25586 | 5/2000 |

OTHER PUBLICATIONS

Anderson, T.H., Alkoxylated Glyceride Emulsifiers in Agricultural Applications, Pesticide Formulations and Application Systems: 21, 2001, 136-146.*
U.S. Appl. No. 11/908,521, filed Sep. 13, 2007, Yoshii, et al.
U.S. Appl. No. 12/280,567, filed Aug. 25, 2008, Yoshii, et al.
U.S. Appl. No. 13/049,169, filed Mar. 16, 2011, Yoshii, et al.

* cited by examiner

*Primary Examiner* — Janet Epps-Smith
*Assistant Examiner* — Yanzhi Zhang
(74) *Attorney, Agent, or Firm* — Oblon, Spivak, McClelland, Maier & Neustadt, L.L.P.

(57) ABSTRACT

A herbicidal composition comprising a herbicidal sulfonylurea compound or its salt, and an alkoxylated glyceride. A method for controlling undesired plants or inhibiting their growth, which comprises applying a herbicidally effective amount of the herbicidal composition to the undesired plants or to a place where they grow. A method for enhancing the herbicidal effect of a herbicidal sulfonylurea compound or its salt by means of an alkoxylated glyceride.

20 Claims, No Drawings

HERBICIDAL COMPOSITION HAVING THE HERBICIDAL EFFECT ENHANCED, AND METHOD FOR ENHANCING THE HERBICIDAL EFFECT

TECHNICAL FIELD

The present invention relates to a herbicidal composition containing a sulfonylurea compound or its salt, as a herbicidally active ingredient, and having the herbicidal effect enhanced.

BACKGROUND ART

Heretofore, various herbicides have been used for the purpose of protecting crop plants, and it has been common to incorporate an adjuvant capable of enhancing their herbicidal effects for the purpose of e.g. reducing the dosage of the herbicidally active ingredient.

GB Patent Publication No. 2309904 discloses a mixture comprising a dicarboxylic acid type compound and an ethoxylated and/or propoxylated triglyceride, and it is disclosed that the herbicidal effect can be enhanced if this mixture is combined with a herbicide. Further, EP 0598515A discloses that the herbicidal effect of a certain specific sulfonylurea compound can be improved by employing an ethoxylated fatty amine type surfactant, and a vegetable oil and/or a mineral oil. However, these references disclose nothing about use of an alkoxylated glyceride to enhance the herbicidal effect of a herbicidal sulfonylurea compound or its salt.

A sulfonylurea herbicide which is commonly and commercially available is one of herbicides having small application dosages. However, from the viewpoint of the environmental problem or economical efficiency, it is desired to further reduce its application dosage. On the other hand, it is possible to reduce the application dosage of a sulfonylurea herbicide by incorporating an adjuvant. However, if the application amount of the adjuvant itself increases, it may adversely affect the environment or the economical efficiency. Thus, it is desired to reduce the application dosages of both the sulfonylurea herbicide and the adjuvant.

Under these circumstances, the present inventors have conducted various studies with an aim to remarkably enhance the herbicidal effect of a sulfonylurea herbicide thereby to reduce its application dosage, and as a result, have accomplished the present invention.

DISCLOSURE OF THE INVENTION

Namely, the present invention provides a herbicidal composition comprising a herbicidal sulfonylurea compound or its salt, and an alkoxylated glyceride; a method for controlling undesired plants by means of such a herbicidal composition; and a method for enhancing the herbicidal effect of a sulfonylurea compound or its salt, by means of an alkoxylated glyceride.

In the present invention, the herbicidal effect of the sulfonylurea compound or its salt can be remarkably improved by the alkoxylated glyceride. Accordingly, it is thereby possible to provide a herbicidal composition having the herbicidal effect remarkably improved, whereby the application dosage of the sulfonylurea compound or its salt can be reduced, and a method for remarkably enhancing the herbicidal effect of the sulfonylurea compound or its salt. Further, the present invention brings about a merit such that the types of plants against which the herbicidal effect extends will increase, or the period for application can be extended.

BEST MODE FOR CARRYING OUT THE INVENTION

The herbicidal composition of the present invention comprises a herbicidal sulfonylurea compound or its salt, and an alkoxylated glyceride. Further, the present invention provides a method for controlling undesired plants or inhibiting their growth, which comprises applying (a) a herbicidally effective amount of a herbicidal sulfonylurea compound or its salt, and (b) an effective amount of an alkoxylated glyceride, to the undesired plants or to a place where they grow. The present invention is carried out, for example, (1) by formulating a sulfonylurea compound or its salt by means of various additives, diluting the formulation together with an alkoxylated glyceride with e.g. water, and applying it to the undesired plants or to a place where they grow, or (2) by formulating a sulfonylurea compound or its salt and an alkoxylated glyceride together with various additives, diluting the formulation with e.g. water or without diluting it, and applying it to the undesired plants or to a place where they grow. In the present invention, in the application to the undesired plants or to a place where they grow, the application to the undesired plants themselves, e.g. the foliar application, is preferred.

In the present invention, the sulfonylurea compound or its salt may be used in combination with one or more other herbicidal compounds. Namely, the present invention can be carried out by a method for controlling undesired plants or inhibiting their growth by such a combined use of other herbicidal compounds, which comprises applying (a) a herbicidally effective amount of a herbicidal sulfonylurea compound or its salt, (b) an effective amount of an alkoxylated glyceride, and (c) a herbicidally effective amount of other herbicidal compound(s), to the undesired plants or to a place where they grow. For example, it may be carried out (1) formulating a sulfonylurea compound or its salt and other herbicidal compound(s) separately or all together, by means of various additives, diluting the formulation together with an alkoxylated glyceride with e.g. water, and applying it to the undesired plants or to a place where they grow, (2) by formulating a sulfonylurea compound or its salt, and an alkoxylated glyceride, together with various additives, diluting the formulation together with a separately formulated other herbicidal compound(s) with e.g. water, and applying it to the undesired plants or to a place where they grow, (3) by formulating a sulfonylurea compound or its salt, other herbicidal compound(s) and an alkoxylated glyceride, together with various additives, diluting the formulation with e.g. water or without diluting it, and applying it to the undesired plants or to a place where they grow, or (4) by formulating other herbicidal compound(s) and an alkoxylated glyceride together with various additives, diluting the formulation together with a separately formulated sulfonylurea compound or its salt with e.g. water, and applying it to the undesired plants or to a place where they grow.

The sulfonylurea compound is a compound having the following partial structure:

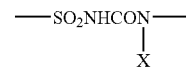

(wherein X is a hydrogen atom or an alkyl group), and it may, for example, be amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucetosulfuron, flupyrsulfuron, foramsulfuron, halosulfuron-methyl, imazosulfuron, iodosulfuron, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, or tritosulfuron. Among them, flazasulfuron, foramsulfuron, nicosulfuron, rimsulfuron, trifloxysulfuron or tritosulfuron is preferred. Among them, nicosulfuron is particularly preferred.

As the salt of such a sulfonylurea compound(s), various types may be mentioned. It may, for example, be a salt with an alkali metal such as sodium or potassium, a salt with an alkaline earth metal such as magnesium or calcium, or a salt with an amine such as monomethylamine, dimethylamine or triethylamine.

The alkoxylated glyceride is one to enhance the herbicidal effect of the sulfonylurea compound or its salt, and it may, for example, be as follows.

As the alkoxylated glyceride, a monoglyceride, a diglyceride and a triglyceride are present, and all of them are included in the present invention.

The alkoxylated glyceride has one or more alkylene oxide moieties at optional positions of the glyceride. Such an alkylene oxide moiety may, for example, be ethylene oxide, propylene oxide, a copolymer thereof or a block copolymer thereof. The average addition molar amount of the alkylene oxide is from 1 to 200 mols, preferably from 2 to 150 mols, more preferably from 10 to 100 mols.

The glyceride moiety of the alkoxylated glyceride may, for example, be a fatty acid ester having glycerin or its derivative bonded with a fatty acid group or its derivative, or a phosphoglyceride having glycerin or its derivative bonded with a phosphoric acid group or its derivative. Particularly preferred is a fatty acid ester having glycerin or its derivative bonded with a fatty acid group or its derivative.

The above glycerin or its derivative may, for example, be a compound represented by the following formula (I):

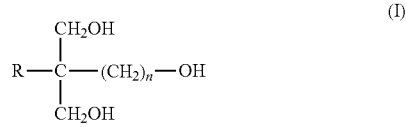

(wherein R is a hydrogen atom or a $C_{1-6}$ alkyl group, and n is an integer of from 0 to 6.)

The above fatty acid group may be either saturated or unsaturated and may be linear or branched, and its carbon number may be from 4 to 24, preferably from 10 to 20. The fatty acid may, for example, be a saturated fatty acid such as butyric acid, n-caproic acid, caprylic acid, n-capric acid, lauric acid, myristic acid, palmitic acid, stearic acid, isostearic acid or arachic acid, or an unsaturated fatty acid such as palmitoleic acid, oleic acid, linoleic acid, linolenic acid, monoctic acid, arachidonic acid or docosahexaenoic acid. Among them, palmitic acid, stearic acid, isostearic acid or oleic acid is, for example, preferred.

The above fatty acid group may be cyclic and may contain one or more hetero atoms in such a cyclic group, or the methylene moiety may be converted to oxo or thioxo. As a specific example, a pyroglutamic acid group may be mentioned. Further, the fatty acid group may be substituted by a hydroxyl group at an optional position. As a specific example, a ricinoleic acid group may be mentioned.

Further, the alkoxylated glyceride may have an alkylene oxide at the terminal of the fatty acid group (on the side opposite to the bonding cite with glycerin), and at the terminal of such an alkylene oxide, a fatty acid group may further be bonded.

The above phosphoglyceride may, for example, be phosphatidylcholine, phosphatidylethanolamine, phosphatidylserine, phosphatidylinositol, phosphatidylglycerol or diphosphatidylglycerol.

The following may, for example, be mentioned as specific examples of the alkoxylated glyceride.

Polyoxyethylene hydrogenated castor oil (tradenames: EMANON CH-25, EMANON CH-80; EMALEX HC-5, EMALEX HC-100; Sorpol HC-10, Sorpol HC-20, Sorpol HC-40, Sorpol HC-50, Sorpol HC-80, Sorpol HC-100, Sorpol HC-150; PEGNOL HC-30; NIKKOL HCO-5, NIKKOL HCO-10, NIKKOL HCO-20, NIKKOL HCO-30, NIKKOL HCO-40, NIKKOL HCO-50, NIKKOL HCO-60, NIKKOL HCO-80, NIKKO HCO-100, etc.)

Polyoxyethyleneglyceryl monostearate (tradenames: EMALEX GM-5, EMALEX GM-40, etc.)

Polyoxyethylene castor oil (tradenames: EMALEX C-20, EMALEX C-50, etc.)

Polyoxyethylene glyceryl triisostearate (tradenames: EMALEX GWIS-303, EMALEX GWIS-340, EMALEX GWIS-360, EMALEX GWIS-340EX, etc.)

Polyoxyethylene glyceryl monoisostearate (tradenames; EMALEX GWIS-103, EMALEX GWIS-115, EMALEX GWIS-125, EMALEX GWIS-160, EMALEX GWIS-160EX, etc.)

Polyoxyethylene glyceryl tristearate (tradenames: EMALEX GWS-303, EMALEX GWS-320, etc.)

Polyoxyethylene glyceryl distearate (tradenames: EMALEX GWS-204, etc.)

Polyoxyethylene glyceryl trioleate (tradename: EMALEX GWO-303, EMALEX GWO-360, etc.)

Polyoxyethylene hydrogenated castor oil monoisostearate (tradenames: EMALEX RWIS-105, EMALEX RWIS-158, EMALEX RWIS-150EX, etc.)

Polyoxyethylene hydrogenated castor oil triisostearate (tradenames: EMALEX RWIS-305, EMALEX RWIS-360, EMALEX RWIS-360EX, etc.)

Polyoxyethylene hydrogenated castor oil monolaurate (tradenames: EMALEX RWL-120, EMALEX RWL-160, etc.)

Polyoxyethylene 1,1,1-trimethylolpropane tristearate (tradenames: EMALEX TPS-303, EMALEX TPS-310, etc.)

Polyoxyethylene 1,1,1-trimethylolpropane trimyristate (tradenames: EMALEX TPM-303, EMALEX TPM-330, etc.)

Polyoxyethylene 1,1,1-trimethylolpropane distearate (tradenames: EMALEX TPS-203, EMALEX TPS-205, etc.)

Polyoxyethylene 1,1,1-trimethylolpropane triisostearate (tradenames: EMALEX TPIS-303, EMALEX TPIS-350, etc.)

Polyoxyethylene hydrogenated castor oil pyroglutamic acid isostearate (tradenames: PYROTER CPI-30, PYROTER CPI-60, etc.)

Polyoxyethylene glyceryl pyroglutamic acid isostearate (tradenames: PYROTER GPI-25, etc.)

Among those represented by the above tradenames, EMANONS are manufactured by Kao Corporation, EMALEX and PYROTER are manufactured by Nihon Emulsion Co., Ltd., Sorpol and PEGNOL are manufactured by TOHO Chemical Industry Co., Ltd., and NIKKOLS are manufactured by NIKKO CHEMICALS CO., LTD.

Among the above alkoxylated glycerides, polyoxyethylene hydrogenated castor oil, polyoxyethylene glyceryl triisostearate, polyoxyethylene glyceryl monoisostearate, polyoxyethylene 1,1,1-trimethylolpropane triisostearate, polyoxyethylene hydrogenated castor oil pyroglutamic acid isostearate, or polyoxyethylene glyceryl pyroglutamic acid isostearate may, for example, be preferred.

As other herbicidal compound(s) which can be used in combination with the sulfonylurea compound or its salt, the compound groups of the following (1) to (10) (common names including those which are applied for ISO) may, for example, be mentioned. Even when not specifically mentioned, in a case where such compounds have salts, alkyl esters or various structural isomers such as optical isomers, they are, of course, all included.

(1) Those which are believed to exhibit herbicidal effects by disturbing hormone activities of plants, such as a phenoxy type such as 2,4-D, 2,4-DP, MCPA, MCPB, MCPP or naproanilide, an aromatic carboxylic acid type such as 2,3,6-TBA, dicamba, dichlobenil, picloram, triclopyr or clopyralid, and others such as benazolin, quinclorac, quinmerac, diflufenzopyr and thiazopyr.

(2) Those which are believed to exhibit herbicidal effects by inhibiting photosynthesis of plants, such as, a urea type such as chlorotoluron, diuron, fluometuron, linuron, isoproturon, metobenzuron or tebuthiuron, a triazine type such as simazine, atrazine, atratone, simetryn, prometryn, dimethametryn, hexazinone, metribuzin, terbuthylazine, cyanazine, ametryn, cybutryne, triaziflam or propazine, a uracil type such as bromacil, lenacil or terbacil, an anilide type such as propanil or cypromid, a carbamate type such as swep, desmedipham or phenmedipham, a hydroxybenzonitrile type such as bromoxynil, bromoxynil-octanoate or ioxynil, and others such as pyridate, bentazon and amicarbazone.

(3) Quaternary ammonium salt type such as paraquat or diquat, which is believed to be converted to free radicals by itself to form active oxygen in the plant body.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen-sodium, fomesafen, oxyfluorfen, lactofen or ethoxyfen-ethyl, a cyclic imide type such as chlorphthalim, flumioxazin, flumiclorac-pentyl or fluthiacet-methyl, and others such as oxadiargyl, oxadiazon, sulfentrazone, carfentrazone-ethyl, thidiazimin, pentoxazone, azafenidin, pyraflufen-ethyl, benzfendizone, butafenacil, metobenzuron, cinidon-ethyl, flupoxam, fluazolate, profluazol and pyrachlonil.

(5) Those which are believed to exhibit herbicidal effects characterized by whitening activities by inhibiting chromogenesis of plants such as carotenoids, such as a pyridazinone type such as norflurazon or metflurazon, a pyrazole type such as pyrazolate, pyrazoxyfen or benzofenap, and others such as amitrol, fluridone, flurtamone, diflufenican, methoxyphenone, clomazone, sulcotrione, mesotrione, isoxaflutole, difenzoquat, isoxachlortole, benzobicyclone, picolinofen and beflubutamid.

(6) Those which exhibit strong herbicidal effects specifically to gramineous plants, such as an aryloxyphenoxypropionic acid type such as diclofop-methyl, flamprop-M-methyl, pyriphenop-sodium, fluazifop-butyl, haloxyfop-methyl, quizalofop-ethyl, cyhalofop-butyl or fenoxaprop-ethyl, and a cyclohexanedione type such as alloxydim-sodium, clethodim, sethoxydim, tralkoxydim, butroxydim, tepraloxydim, caloxydim or clefoxydim.

(7) Those which are believed to exhibit herbicidal effects by inhibiting an amino acid biosynthesis of plants, such as a triazolopyrimidinesulfonamide type such as flumetsulam, metosulam, diclosulam, cloransulam-methyl, florasulam, metosulfam or penoxsulam, an imidazolinone type such as imazapyr, imazethapyr, imazaquin, imazamox, imazameth, imazamethabenz or imazapic, a pyrimidinylsalicylic acid type such as pyrithiobac-sodium, bispyribac-sodium, pyriminobac-methyl, pyribenzoxim or pyriftalid, a sulfonylaminocarbonyltriazolinone type such as flucarbazone or procarbazone-sodium, and others such as glyphosate-ammonium, glyphosate-isopropylamine, glufosinate-ammonium and bialaphos.

(8) Those which are believed to exhibit herbicidal effects by inhibiting cell mitoses of plants, such as a dinitroaniline type such as trifluralin, oryzalin, nitralin, pendimethalin or ethalfluralin, an organic phosphorus type such as amiprofosmethyl, butamifos, anilofos or piperophos, a phenylcarbamate type such as chlorpropham or barban, a cumylamine type such as daimuron, cumyluron or bromobutide, and others such as asulam, dithiopyr and thiazopyr.

(9) Those which are believed to exhibit herbicidal effects by inhibiting protein biosynthesis or lipid biosynthesis of plants, such as, a thiocarbamate type such as EPTC, butylate, molinate, dimepiperate, fluazolate, esprocarb, thiobencarb, pyributicarb or trialate, a chloroacetamide type such as alachlor, butachlor, pretilachlor, metolachlor, S-metolachlor, thenylchlor, pethoxamid, dimethenamid, acetochlor or propachlor, and others such as etobenzanid, mefenacet, flufenacet, tridiphane, cafenstrole, fentrazamide, oxaziclomefone and indanofan.

(10) Those which are believed to exhibit herbicidal effects by being parasitic on plants, such as *Xanthomonas campestris, Epicoccosurus nematosurus, Exserohilum monoseras* and *Drechsrela monoceras.*

In the present invention, a coadjuvant may be employed, as the case requires for the purpose of more distinctly enhancing the herbicidal effects of the sulfonylurea compound or its salt, increasing the types of plants against which the herbicidal effects are effective, or expanding the application period.

As such a coadjuvant, a chelating agent, a nitrogen-containing fertilizer or a cationic surfactant may, for example, be mentioned. Among them, a chelating agent or a nitrogen-containing fertilizer is preferred. When coadjuvants are to be applied, two or more of them may suitably be used in combination, as the case requires.

Specific examples of the chelating agent include aminopolycarboxylic acids and aliphatic carboxylic acids. The aminopolycarboxylic acids may, for example, be ethylenediaminetetraacetic acid (EDTA), iminodiacetic acid (IDA), nitrilotriacetic acid (NTA), ethylene glycol bis(2-aminoethyl ether)-N,N,N',N'-tetraacetic acid (EGTA), diethylenetriamine-N,N,N'',N''-pentaacetic acid (DTPA), cyclohexanediaminetetraacetic acid (CDTA), or their salts. Further, the aliphatic carboxylic acids may, for example, be citric acid, malic acid, oxalic acid, lactic acid, gluconic acid, heptonic acid, or their salts. Two or more of them may suitably be used in combination, as the case requires.

Specific examples of the nitrogen-containing fertilizer include ammonium salts such as ammonium sulfate, ammonium chloride, ammonium phosphite and ammonium phosphate; and nitrates such as ammonium nitrate, potassium nitrate and calcium nitrate. Two or more of them may suitably be used in combination, as the case requires.

Specific examples of the cationic surfactant include tertiary amines such as alkoxylated fatty acid amines; salts of tertiary amines; and quaternary ammonium salts. Two or more of them may suitably be used in combination, as the case requires.

As the above-mentioned salts of amino polycarboxylic acids or aliphatic carboxylic acids, various salts may be mentioned. For example, a salt with an alkali metal such as sodium or potassium, a salt with an alkaline earth metal such as magnesium or calcium, or a salt with an amine such as monomethylamine, dimethylamine or triethylamine, may be mentioned.

In the present invention, the blend ratio of the sulfonylurea compound or its salt to the alkoxylated glyceride cannot generally be defined, since it may be suitably changed depending upon the type of the sulfonylurea compound or the alkoxylated glyceride, the formulation, the climate condition, the type or size of the plants to be controlled, etc. However, it may, for example, be within a range of from 16:1 to 1:6000, more preferably from 8:1 to 1:1000, further preferably from 2:1 to 1:600, still further preferably from 1:2 to 1:50, by weight ratio.

In a case where a coadjuvant is used in the present invention, the blend ratio cannot generally be defined, since it may be suitably changed depending upon the type of the sulfonylurea compound, the type of the alkoxylated glyceride, the type of the coadjuvant, the formulation, the climate conditions, the type and size of the plants to be controlled, etc. However, the blend ratio of the alkoxylated glyceride and the coadjuvant may, for example, be within a range of from 4000:1 to 1:5, preferably from 500:1 to 2:1, by weight ratio.

Further, if the blend ratio is represented for each mode of practical applications, the following may, for example, be mentioned. (1) In a case where the sulfonylurea compound or its salt is formulated by means of various additives, then diluted together with the alkoxylated glyceride with e.g. water and applied to undesired plants or to a place where they grow, and the formulated sulfonylurea compound or its salt and alkoxylated glyceride are diluted with from 10 to 3000 liters/ha, preferably from 50 to 2000 liters/ha, more preferably from 100 to 1000 liters/ha, of water, the alkoxylated glyceride is added in an amount of from 0.005 to 4 wt %, preferably from 0.01 to 2 wt %, more preferably from 0.02 to 0.5 wt %, based on the diluted liquid. (2) In a case where the sulfonylurea compound or its salt, and the alkoxylated glyceride, are formulated together with various additives, then diluted with e.g. water or without dilution, and applied to undesired plants or to a place where they grow, the sulfonylurea compound or its salt, and the alkoxylated glyceride, may be blended so that their ratio will be in the above-mentioned weight ratio range. (3) In a case where one or more other herbicidal compounds are used in combination with the sulfonylurea compound or its salt, such can be carried out in accordance with the blend ratio in the above case (1) or (2). (4) In a case where a coadjuvant is further employed and they are diluted with water in the same manner as described above, in each of the above cases (1), (2) and (3), it may be added in an amount of from 0.0001 to 0.05 wt %, preferably from 0.001 to 0.01 wt %, based on the diluted liquid.

In the present invention, (1) in a case where the sulfonylurea compound or its salt, and other herbicidal compound(s), are, separately or together, formulated by means of various additives, (2) in a case where the sulfonylurea compound or its salt, and the alkoxylated glyceride, are formulated together with various additives, (3) in a case where the sulfonylurea compound or its salt, other herbicidal compound(s) and the alkoxylated glyceride, are formulated together with various additives, or (4) in a case where the sulfonylurea compound or its salt, other herbicidal compound(s), the alkoxylated glyceride and the coadjuvant, are formulated together with various additives, they may be formulated into various formulations. For example, various formulations such as a wettable powder, water-dispersible granules, a water-based suspension concentrate, an oil-based suspension concentrate, a gel formulation, an emulsifiable concentrate, water soluble granules, an emulsion, a microemulsion, a suspoemulsion, and a multiple emulsion, may be mentioned. Various additives which can be used here may be any additives so long as they are commonly used in this technical field, and for example, a surfactant, a carrier, a solvent, a vegetable oil, a mineral oil, an anti-settling agent, a thickener, an antifoaming agent, an antifreezing agent, an antioxidant, an oil absorbent, a gelling agent, a filler, a dispersion stabilizer, a phytotoxicity reducing agent, an anti-mold agent, a binder, a stabilizer, a disintegrator, a preservative, and an inorganic ammonium salt, may be mentioned. The following may, for example, be mentioned as specific examples of such various additives. Further, such formulations may be prepared in accordance with methods commonly employed in this technical field.

The surfactant includes, for example, anionic surfactants such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a polyoxyethylene styrylaryl ether sulfate, an ammonium polyoxyethylene styrylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a polyoxyethylene styrylaryl ether phosphoric acid ester or its salt, a salt of a condensate of naphthalene sulfonate with formalin and a salt of a condensate of alkylnaphthalene sulfate with formalin; nonionic surfactants such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester, and cationic surfactants such as an alkoxylated fatty acid amine. If desired, two or more of them may suitably be used in combination.

The carrier or the filler may, for example, be diatomaceous earth, slaked lime, calcium carbonate, talc, white carbon, kaoline, bentonite, a mixture of kaolinite and sericite, clay, sodium carbonate, sodium bicarbonate, mirabilite, zeolite, starch, sodium chloride, ammonium phosphate, ammonium sulfate, ammonium chloride, sugar, urea, lactose, or glucose. If desired, two or more of them may suitably be used in combination.

The solvent may, for example, be water, solvent naphtha, paraffin, dioxane, acetone, isophorone, methyl isobutyl ketone, chlorobenzene, cyclohexane, dimethyl sulfoxide, dimethyl formamide, N-methyl-2-pyrrolidone, an alcohol, acetic acid, butyric acid, isopropyl acetate, butyl acetate, benzene, an alkylbenzene or an alkylnaphthalene. If desired, two or more of them may suitably be used in combination.

The vegetable oil may, for example, be olive oil, kapok oil, castor oil, papaya oil, camellia oil, coconut oil, sesame oil, corn oil, rice bran oil, peanut oil, cottonseed oil, soybean oil, rapeseed oil, linseed oil, tung oil, sunflower oil, safflower oil, or a fatty acid derived from each of the above-mentioned oils or an alkyl ester of such a fatty acid. The mineral oil may, for example, be an aliphatic hydrocarbon such as liquid paraffin or paraffinic petroleum, or an aromatic hydrocarbon such as an alkyl benzene or an alkyl naphthalene. If desired two or more of them may suitably be used in combination. The above fatty acid may, for example, be a $C_{12-22}$ saturated or unsaturated fatty acid, such as lauric acid, palmitic acid, stearic acid, oleic acid, linolic acid, linoleic acid, erucic acid or brassidic acid, and the alkyl ester thereof may, for example, a $C_{1-18}$ linear or branched alkyl ester, such as a methyl ester, a butyl ester, an isobutyl ester or an oleyl ester.

The anti-settling agent may, for example, be silica, an organic bentonite (bentonite-alkylamino complex), bentonite, white carbon or aluminum magnesium silicic acid. If desired, two or more of them may be suitably used in combination.

The thickener may, for example, be a heteropolysaccharide such as xanthan gum or guar gum, a water-soluble polymer such as polyvinyl alcohol, a sodium salt of carboxymethyl cellulose or sodium alginate, bentonite or white carbon. If desired, two or more of them may suitably be used in combination.

The antifoaming agent may, for example, be polydimethylsiloxane or acetylene alcohol. If desired, two or more of them may suitably be used in combination.

The antifreezing agent may, for example, be ethylene glycol, propylene glycol, glycerin or urea. If desired, two or more of them may suitably be used in combination.

The oil-absorber may, for example, be silicon dioxide, hydrolyzed starch, kaoline, clay, talc, diatomaceous earth, a synthesized product of diatomaceous earth/lime, asbestos, a mixture of kaolinite and sericite, calcium silicate, calcium carbonate, calcium carbonate silicate, acid clay, carbon black, graphite, a pearlite processed product, alumina, titanium dioxide, basic magnesium carbonate, magnesium silicate aluminate, silica-alumina filler or magnesium silicate hydrate. If desired, two or more of them may suitably be used in combination.

The gelling agent may, for example, be silica, organic attapulgite, clay, hydrogenated castor oil, a higher fatty acid ester, a higher alcohol, a salt of dialkyl sulfosuccinic acid ester, a benzoate, an alkyl sulfate, a poly acrylic polymer, or a mixture of a poly acrylic acid co-polymer and water, or 12-hydroxystearic acid. If desired, two or more of them may suitably be used in combination.

The binder may, for example, be lignin sulfonic acid, xanthan gum, carboxymethylcellulose or starch. If desired, two or more of them may suitably be used in combination.

The stabilizer may, for example, be urea.

The disintegrator may, for example, be a calcium salt of carboxymethylcellulose, an inorganic salt such as ammonium sulfate, potassium chloride or magnesium chloride, and one showing a disintegrating activity among the above-mentioned surfactants, such as sodium lauryl sulfate, sodium dodecylbenzene sulfonate, or an ammonium polyacrylate. If desired, two or more of them may suitably be used in combination.

The preservative may, for example, be formalin, p-chloro m-xylenol or 1,2-benzisothiazolin-3-one. If desired, two or more of them may suitably be used in combination.

In the above-mentioned various formulations, the blend proportions of various components cannot generally be defined, since they may suitably be changed depending upon the types of the blend components, the formulations or the application sites. However, a formulation may, for example, be prepared by incorporating the sulfonylurea compound or its salt in a proportion of from 0.1 to 95 parts by weight, preferably from 2 to 85 parts by weight and incorporating, as the rest, various additives in a proportion of from 5 to 99.9 parts by weight, preferably from 15 to 98 parts by weight. Further, in a case where the alkoxylated glyceride is incorporated in a proportion of from 0.1 to 94.9 parts by weight, preferably from 5 to 60 parts by weight, as the case requires, where other herbicidal compound(s) are incorporated in a proportion of from 0.1 to 94.9 parts by weight, preferably from 0.5 to 75 parts by weight, as the case requires, or where the coadjuvant is incorporated in a proportion of from 0.1 to 94.9 parts by weight, preferably from 0.2 to 60 parts by weight, as the case requires, a formulation may be prepared by incorporating various additives as the rest, so that the total would be 100 parts by weight. Now, the blend proportions of the respective components in some formulations will be exemplified below, but it should be understood that the present invention is by no means restricted to such specific formulations.

In the case of a wettable powder, a formulation may be prepared by incorporating the sulfonylurea compound or its salt in a proportion of from 0.1 to 95 parts by weight, preferably from 5 to 85 parts by weight, blending a surfactant in a proportion of from 0.5 to 40 parts by weight, preferably from 5 to 30 parts by weight, and blending as the rest, the carrier or filler in a proportion of from 4.5 to 99.4 parts by weight, preferably from 10 to 90 parts by weight. Further, in a case where the alkoxylated glyceride is incorporated in a proportion of from 0.1 to 94.9 parts by weight, preferably from 10 to 60 parts by weight, as the case requires, where other herbicidal compound(s) are incorporated in a proportion of from 0.1 to 94.9 parts by weight, preferably from 0.5 to 75 parts by weight, as the case requires, where a coadjuvant is incorporated in a proportion of from 0.1 to 94.9 parts by weight, preferably from 0.2 to 60 parts by weight, as the case requires, or where an oil absorbent is incorporated in a proportion of from 1 to 90 parts by weight, preferably from 1 to 50 parts by weight, as the case requires, a formulation may be prepared by incorporating a carrier or filler as the rest, so that the total would be 100 parts by weight.

In the case of water-dispersible granules, a formulation may be prepared by incorporating the sulfonylurea compound or its salt in a proportion of from 0.1 to 95 parts by weight, preferably from 5 to 85 parts by weight, and the surfactant in a proportion of from 0.5 to 40 parts by weight, preferably from 5 to 30 parts by weight, and incorporating, as the rest, a carrier or filler in a proportion of from 4.5 to 99.4 parts by weight, preferably from 10 to 90 parts by weight. Further, in a case where the alkoxylated glyceride is incorporated in a proportion of from 0.1 to 94.9 parts by weight, preferably from 10 to 60 parts by weight, as the case requires, where other herbicidal compound(s) are incorporated in a proportion of from 0.1 to 94.9 parts by weight, preferably from 0.5 to 75 parts by weight, as the case requires, where the coadjuvant is incorporated in a proportion of from 0.1 to 94.9 parts by weight, preferably from 0.2 to 60 parts by weight, as the case requires, where a binder is incorporated in a proportion of from 0.1 to 10 parts by weight, preferably from 0.5 to 5 parts by weight, as the case requires, where a disintegrator is incorporated in a proportion of from 0.1 to 40 parts by weight, preferably from 0.5 to 20 parts by weight, as the case requires, or where an oil absorbent is incorporated in a proportion of from 1 to 90 parts by weight, preferably from 1 to 50 parts by weight, as the case requires, a formulation may be prepared by incorporating, as the rest, a carrier or filler, so that the total would be 100 parts by weight.

In the case of a water-based suspension concentrate, a formulation may be prepared by incorporating the sulfonylurea compound or its salt in a proportion of from 0.1 to 60 parts by weight, preferably from 2 to 50 parts by weight, and a surfactant in a proportion of from 0.5 to 20 parts by weight, preferably from 1 to 15 parts by weight, and incorporating, as the rest, water in a proportion of from 25 to 99.4 parts by weight, preferably from 30 to 97 parts by weight. Further, in a case where the alkoxylated glyceride is incorporated in a proportion of from 0.1 to 60 parts by weight, preferably from 5 to 40 parts by weight, as the case requires, where other herbicidal compound(s) are incorporated in a proportion of from 0.1 to 60 parts by weight, preferably from 0.5 to 30 parts by weight, as the case requires, where a coadjuvant is incorporated in a proportion of from 0.1 to 60 parts by weight, preferably from 0.2 to 40 parts by weight, as the case requires, where an antifoaming agent is incorporated in a proportion of from 0.05 to 3 parts by weight, preferably from 0.1 to 1 parts by weight, as the case requires, where an anti-freezing agent is incorporated in a proportion of from 0.5 to 10 parts by weight, preferably from 2 to 10 parts by weight, as the case requires, where an anti-settling agent is incorporated in a proportion of from 0.1 to 5 parts by weight, preferably from 0.5 to 3 parts by weight, as the case requires, where a thickener is incorporated in a proportion of from 0.1 to 5 parts by weight, preferably from 0.1 to 2 parts by weight, as the case requires, or where a preservative is incorporated in a proportion of from 0.01 to 1 part by weight, preferably from 0.05 to 0.2 part by weight, as the case requires, a formulation may be prepared by incorporating water as the rest, so that the total would be 100 parts by weight.

In the case of an oil-based suspension concentrate, a formulation may be prepared by incorporating the sulfonylurea compound or its salt in a proportion of from 0.1 to 40 parts by weight, preferably from 2 to 35 parts by weight, and a surfactant in a proportion of from 1 to 30 parts by weight, preferably from 1 to 25 parts by weight, and incorporating, as the rest, a vegetable or mineral oil in a proportion of from 10 to 98.9 parts by weight, preferably from 20 to 97 parts by weight. Further, in a case where the alkoxylated glyceride is incorporated in a proportion of from 0.1 to 80 parts by weight, preferably from 5 to 60 parts by weight, as the case requires, where other herbicidal compound(s) are incorporated in a proportion of from 0.1 to 40 parts by weight, preferably from 0.5 to 30 parts by weight, as the case requires, where a coadjuvant is incorporated in a proportion of from 0.1 to 40 parts by weight, preferably from 0.2 to 35 parts by weight, as the case requires, where an anti-settling agent is incorporated in a proportion of from 0.1 to 5 parts by weight, preferably from 0.5 to 3 parts by weight, as the case requires, or where a stabilizer is incorporated in a proportion of from 0.1 to 20 parts by weight, preferably from 1 to 10 parts by weight, as the case requires, a formulation may be prepared by incorporating a vegetable oil or mineral oil as the rest, so that the total would be 100 parts by weight.

In the case of a gel formulation, a formulation may be prepared by incorporating the sulfonylurea compound or its salt in a proportion of from 0.1 to 40 parts by weight, preferably from 2 to 30 parts by weight, a surfactant in a proportion of from 1 to 30 parts by weight, preferably from 1 to 15 parts by weight, and a gelling agent in a proportion of from 0.1 to 50 parts by weight, preferably from 5 to 40 parts by weight, and incorporating, as the rest, a vegetable oil or mineral oil in a proportion of from 10 to 98.8 parts by weight, preferably from 20 to 92 parts by weight. Further, in a case where the alkoxylated glyceride is incorporated in a proportion of from 0.1 to 60 parts by weight, preferably from 5 to 25 parts by weight, as the case requires, where other herbicidal compound(s) are incorporated in a proportion of from 0.1 to 30 parts by weight, preferably from 0.5 to 20 parts by weight, as the case requires, where a coadjuvant is incorporated in a proportion of from 0.1 to 40 parts by weight, preferably from 0.2 to 30 parts by weight, as the case requires, or where an anti-settling agent is incorporated in a proportion of from 0.1 to 3 parts by weight, preferably from 0.5 to 2 parts by weight, as the case requires, a formulation may be prepared by incorporating a vegetable oil or mineral oil as the rest, so that the total would be 100 parts by weight.

The herbicidal composition of the present invention is capable of controlling a wide range of weeds including, for example, sedge (or Cyperaceae) such as rice flatsadge (*Cyperus iria* L.) or purple nutsadge (*Cyperus rotundus* L.), grasses (or gramineae) such as barnyardgrass (*Echinochloa crusgalli* L.), crabgrass (*Digitaria sanguinalis* L.), green foxtail (*Setaria viridis* L.), goosegrass (*Eleusine indica* L.), wild oat (*Avena fatua* L.), johnsongrass (*Sorghum halepense* L.) or quackgrass (*Agropyron repens* L.), and broadleaves such as velvetleaf (*Abutilon theophrasti* MEDIC.), tall morning glory (*Ipomoea purpurea* L.), common lambsquarters (*Chenopodium album* L.), prickly sida (*Sida spinosa* L.), common purslane (Portulaca oleracea L.), redroot pigweed (*Amaranthus retroflexus* L.), sicklepod (*Cassia obtusifolia* L.), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) or three seeded copperleaf (*Acalypha australis* L.), or inhibiting their growth, by applying it to such undesired plants or to a place where they grow, for example, by foliar application. Accordingly, its application range extends not only to crop plant fields but also agricultural fields such as orchards or mulberry fields and non-agricultural fields such as forest land, farm roads, play grounds, factory sites or grass plots. The sulfonylurea compound or its salt may be applied in an amount of 1 to 500 g/ha, preferably from 2 to 250 g/ha. Particularly, a herbicidal composition comprising nicosulfuron or its salt, and an alkoxylated glyceride, is capable of controlling noxious weeds or inhibiting their growth without presenting phytotoxicity to corn, and it is very useful as a herbicidal composition for corn fields. Nicosulfuron may be applied in an amount of from 2 to 400 g/ha, preferably from 5 to 200 g/ha. Further, it may be used in combination or admixture with other agricultural chemicals, fertilizers, phytotoxicity-reducing agents, etc., whereby it is expected to exhibit better effects or activities.

Some preferred embodiments of the present invention will be exemplified. However, the present invention is by no means restricted thereto.

(1) The above herbicidal composition comprising a) a herbicidally effective amount of the sulfonylurea compound or its salt, and b) the alkoxylated glyceride in an effective amount to enhance the herbicidal activity.

(2) The above herbicidal composition comprising a) the sulfonylurea compound or its salt, b) the alkoxylated glyceride in an effective amount to enhance the herbicidal activity, and c) the coadjuvant in an effective amount to enhance the herbicidal activity.

(3) The above herbicidal composition characterized in that the sulfonylurea compound or its salt, and the alkoxylated glyceride, are formulated together with additives.

(4) The above herbicidal composition characterized in that the sulfonylurea compound or its salt, the alkoxylated glyceride and the coadjuvant are formulated (5) together with additives.

(5) The above herbicidal composition characterized in that it comprises the sulfonylurea compound or its salt, and the alkoxylated glyceride, and it is in the form of a water-diluted liquid which can be applied to undesired plants or to a place where they grow.

(6) The above herbicidal composition characterized in that it comprises the sulfonylurea compound or its salt, the alkoxylated glyceride and the coadjuvant, and it is in the form of a water-diluted liquid which can be applied to undesired plants or to a place where they grow.

(7) The above herbicidal composition which further contains a herbicidally effective amount of other herbicidal compound(s).

(8) The above herbicidal composition characterized in that the herbicidal effect of the sulfonylurea compound or its salt is enhanced by the alkoxylated glyceride.

(9) The above herbicidal composition characterized in that the herbicidal effect of the sulfonylurea compound or its salt, is enhanced by the alkoxylated glyceride and the coadjuvant.

(10) The above herbicidal composition characterized in that the herbicidal effect of the herbicidal composition comprising the sulfonylurea compound or its salt and other herbicidal compound(s), is enhanced by the alkoxylated glyceride.

(11) The above herbicidal composition characterized in that the herbicidal effect of the herbicidal composition comprising the sulfonylurea compound or its salt, and other herbicidal compound(s), is enhanced by the alkoxylated glyceride and the coadjuvant.

(12) The above-mentioned method for controlling undesired plants or inhibiting their growth, which comprises applying a) a herbicidally effective amount of the sulfonylurea compound or its salt, and b) the alkoxylated glyceride in an effective amount to enhance the herbicidal activity, to undesired plants or to a place where they grow.

(13) The above method for controlling undesired plants or inhibiting their growth, which comprises applying a) a herbicidally effective amount of the sulfonylurea compound or its salt, b) the alkoxylated glyceride in an effective amount to enhance the herbicidal activity, and c) the coadjuvant in an effective amount to enhance the herbicidal activity, to undesired plants or to a place where they grow.

(14) The above method for controlling undesired plants or inhibiting their growth, which comprises formulating the sulfonylurea compound or its salt by means of various additives, diluting it together with the alkoxylated glyceride with water, and applying it to undesired plants or to a place where they grow.

(15) The above method for controlling undesired plants or inhibiting their growth, which comprises formulating the sulfonylurea compound or its salt by means of various additives, diluting it together with the alkoxylated glyceride and the coadjuvant with water, and applying it to the undesired plants or to a place where they grow.

(16) The above method for controlling undesired plants or inhibiting their growth, which comprises formulating the sulfonylurea compound or its salt, and the alkoxylated glyceride, together with various additives, diluting it with water and applying it to undesired plants or to a place where they grow.

(17) The above method for controlling undesired plants or inhibiting their growth, which comprises formulating the sulfonylurea compound or its salt, the alkoxylated glyceride and the coadjuvant together with various additives, diluting it with water, and applying it to the undesired plants or to a place where they grow.

(18) The above method for controlling undesired plants or inhibiting their growth, characterized by applying foliar application to the undesired plants.

(19) The above method for controlling undesired plants or inhibiting their growth, wherein a herbicidally effective amount of other herbicidal compound(s) are further contained.

(20) The above method for enhancing the herbicidal effect of the sulfonylurea compound or its salt by means of the alkoxylated glyceride in an effective amount to enhance the herbicidal activity.

(21) The above method for enhancing the herbicidal effect of the sulfonylurea compound or its salt by means of the alkoxylated glyceride in an effective amount to enhance the herbicidal activity and the coadjuvant in an effective amount to enhance the herbicidal activity.

(22) The above method for enhancing the herbicidal effect of the herbicidal composition comprising the sulfonylurea compound or its salt, and other herbicidal compound(s) by means of the alkoxylated glyceride in an effective amount to enhance the herbicidal activity and the coadjuvant in an effective amount to enhance the herbicidal activity.

EXAMPLES

Example 1

(1) Nicosulfuron (purity: 93.6%): 81.78 parts by weight
(2) Condensate of sodium alkylnaphthalene sulfonate with formalin (tradename: Supragil MNS/90, manufactured by Rhodia Nicca, Ltd.): 5 parts by weight
(3) Sodium dodecylbenzene sulfonate (tradename: Neogen Powder, manufactured by DAI-ICHI KOGYO SEIYAKU CO., LTD.): 13.22 parts by weight The above components were uniformly mixed, and water was added thereto, followed by kneading, then extrusion granulation, drying and size adjustment to obtain water-dispersible granules. The water-dispersible granules were diluted together with an alkoxylated glyceride with water and then applied.

Example 2

[1]
(1) Sodium dodecylbenzenesulfonate (tradename: Sorpol 5060, manufactured by TOHO Chemical Industry Co., Ltd.): 2 parts by weight
(2) Polyoxyethylene nonylphenyl ether sulfate (tradename: Sorpol 5073, manufactured by TOHO Chemical Industry Co., Ltd.): 3 parts by weight
(3) Polyoxyethylene dodecylphenyl ether (tradename: Noigen EA-33, manufactured by DAI-ICHI KOGYO SEIYAKU CO., LTD.): 1 part by weight
(4) Clay (tradename: hydrated clay, manufactured by TODOROKI SANGYO CO., LTD.): 78 parts by weight
(5) White carbon (tradename: Carplex #80, manufactured by Shionogi & Co., Ltd.): 16 parts by weight The above components were mixed to obtain a blend [A].

[2]
(1) Foramsulfuron (purity: 99.6%): 10 parts by weight
(2) Blend [A]: 90 parts by weight The above components were mixed to obtain a wettable powder. The wettable powder was diluted together with an alkoxylated glyceride with water, and then applied.

Example 3

(1) Tritosulfuron (purity: at least 98%): 10 parts by weight
(2) Blend [A] obtained in the above Example 2: 90 parts by weight The above components were mixed to obtain a wettable powder. The wettable powder was diluted together with an alkoxylated glyceride with water, and then applied.

Example 4

(1) Nicosulfuron (purity: 94.3%): 10.7 parts by weight
(2) Polycarboxylate (tradename: Geropon T/36, manufactured by Rhodia Nicca, Ltd.): 3 parts by weight
(3) Supragil MNS/90 (tradename): 4.3 parts by weight
(4) Sodium alkylnaphthalenesulfonate (tradename: Supragil WP, manufactured by Rhodia Nicca, Ltd.): 2 parts by weight
(5) Carplex #80 (tradename): 33.3 parts by weight
(6) Polyoxyethylene hydrogenated castor oil (tradename: EMANON CH-25, manufactured by Kao Corporation): 46.7 parts by weight EMANON CH-25 was adsorbed on Carplex #80, and then other components were mixed thereto to obtain a wettable powder.

Example 5

(1) Nicosulfuron (purity: 94.3%): 10.7 parts by weight
(2) Supragil MNS/90 (tradename): 5 parts by weight
(3) Neogen Powder (tradename): 14.3 parts by weight
(4) Carplex #80 (tradename): 35 parts by weight
(5) Polyoxyethylene hydrogenated castor oil (tradename: EMANON CH-80, manufactured by Kao Corporation): 35 parts by weight Molten EMANON CH-80 was adsorbed on Carplex #80, and then other components were mixed thereto. Water was added thereto, followed by kneading, then extrusion granulation, drying and size adjustment to obtain water-dispersible granules.

Example 6

(1) Nicosulfuron (purity: 94.3%): 10.7 parts by weight
(2) Supragil MNS/90 (tradename): 5 parts by weight
(3) Neogen Powder (tradename): 12.3 parts by weight
(4) Sodium lignin sulfonate (tradename: New Kalgen WG-4, manufactured by TAKEMOTO OIL & FAT CO., LTD.): 2 parts by weight
(5) Carplex #80 (tradename): 35 parts by weight
(6) Polyoxyethylene hydrogenated castor oil pyroglutamic acid isostearate (tradename: PYROTER CPI-60, manufactured by Nihon Emulsion Co., Ltd.): 35 parts by weight Molten PYROTER CPI-60 was adsorbed on Carplex #80, and then other components were mixed thereto. Water was added thereto, followed by kneading, then extrusion granulation, drying and size adjustment to obtain water-dispersible granules.

Example 7

(1) Nicosulfuron (purity: 94.3%): 10.7 parts by weight
(2) Supragil MNS/90 (tradename): 5 parts by weight
(3) Calcium dodecylbenzenesulfonate (tradename: Rhodacal 70, manufactured by Rhodia Nicca, Ltd.): 4 parts by weight
(4) Bentonite (tradename: KUNIGEL V1, manufactured by Kunimine Industries Co., Ltd.): 10.3 parts by weight
(5) Carplex #80 (tradename): 35 parts by weight
(6) Polyoxyethylene glyceryl triisostearate (tradename: EMALEX GWIS-360, manufactured by Nihon Emulsion Co., Ltd.): 35 parts by weight Molten EMALEX GWIS-360 was adsorbed on Carplex #80, and then other components were mixed thereto. Water was added thereto, followed by kneading, then extrusion granulation, drying and size adjustment to obtain water-dispersible granules.

Example 8

(1) Nicosulfuron (purity: 93.4%): 5.35 parts by weight
(2) Polyoxyethylenetristyrylphenyl ether phosphoric acid ester (tradename: Soprophor 3D33, manufactured by Rhodia Nicca, Ltd.): 5 parts by weight
(3) Polydimethylsiloxane (tradename: Rhodorsil antifoam 432, manufactured by Rhodia Nicca, Ltd.): 0.1 part by weight
(4) Propylene glycol: 5 parts by weight
(5) Water: 54.55 parts by weight
(6) EMANON CH-25 (tradename): 30 parts by weight The above components were mixed and wet-pulverized for 5 minutes by a wet-grinding machine, to obtain a water-based suspension concentrate.

Example 9

(1) Nicosulfuron (purity: 93.4%): 32.11 parts by weight
(2) Soprophor 3D33 (tradename): 5 parts by weight
(3) Rhodorsil antifoam 432 (tradename): 0.1 parts by weight
(4) Propylene glycol: 5 parts by weight
(5) Water: 37.79 parts by weight
(6) EMANON CH-25 (tradename): 20 parts by weight The above components were mixed and wet-pulverized for 5 minutes by a wet-grinding machine to obtain a water-based suspension concentrate.

Example 10

(1) Nicosulfuron (purity: 93.4%): 4.93 parts by weight
(2) A mixture of polyoxyethylene hydrogenated castor oil and dioctyl sulfosuccinate: 10.46 parts by weight
(3) Bentonite-alkylamino complex (tradename: New D Orben, manufactured by SHIRAISHI KOGYO KAISHA, LTD.): 1.05 parts by weight
(4) Corn oil: 62.64 parts by weight
(5) EMANON CH-25 (tradename): 20.92 parts by weight The above components were mixed and wet-pulverized for 15 minutes by a wet-grinding machine to obtain an oil-based suspension concentrate.

Example 11

(1) Nicosulfuron (purity: 93.4%): 7.38 parts by weight
(2) A mixture of polyoxyethylene hydrogenated castor oil and dioctyl sulfosuccinate: 10.46 parts by weight
(3) New D Orben (tradename): 1.05 parts by weight
(4) Corn oil: 49.73 parts by weight
(5) EMANON CH-25 (tradename): 31.38 parts by weight The above components were mixed and wet-pulverized for 15 minutes by a wet-grinding machine to obtain an oil-based suspension concentrate.

Example 12

(1) Nicosulfuron (purity: 93.4%): 4.93 parts by weight
(2) A mixture of polyoxyethylene hydrogenated castor oil and dioctyl sulfosuccinate: 10.46 parts by weight
(3) New D Orben (tradename): 0.53 parts by weight
(4) Urea: 2.09 parts by weight
(4) Corn oil: 61.07 parts by weight
(5) EMANON CH-25 (tradename): 20.92 parts by weight The above components were mixed and wet-pulverized for 15 minutes by a wet-grinding machine, to obtain an oil-based suspension concentrate.

Example 13

(1) Nicosulfuron (purity: 93.4%): 11.7 parts by weight
(2) A mixture of polyoxyethylene hydrogenated castor oil and an alkyl aryl sulfonate: 10 parts by weight
(3) Aromatic hydrocarbon solvent (tradename: Solvesso 150, manufactured by EXXON CHEMICAL): 28.3 parts by weight
(4) EMANON CH-25 (tradename): 50 parts by weight The above components were mixed and wet-pulverized for 10 minutes by a wet-grinding machine, to obtain an oil-based suspension concentrate.

Example 14

(1) Nicosulfuron (purity: 93.4%): 11.7 parts by weight
(2) A mixture of polyoxyethylene hydrogenated castor oil and an alkyl aryl sulfonate: 10 parts by weight
(3) Urea: 3 parts by weight
(4) Solvesso 150 (tradename): 25.3 parts by weight
(5) EMANON CH-25 (tradename): 50 parts by weight The above components were mixed and wet-pulverized for 10 minutes by a wet-grinding machine, to obtain an oil-based suspension concentrate.

Example 15

[1]
(1) Nicosulfuron (purity: 93.4%): 4.93 parts by weight
(2) A mixture of polyoxyethylene hydrogenated castor oil and dioctyl sulfosuccinate: 10.46 parts by weight
(3) New D Orben (tradename): 1.05 parts by weight
(4) Corn oil: 62.64 parts by weight
(5) EMANON CH-25 (tradename): 20.92 parts by weight The above components were mixed and wet-pulverized for 15 minutes by a wet-grinding machine, to obtain a blend [B].

[2]
(1) A mixture of sodium dioctylsulfosuccinate and sodium benzoate (tradename: New Kalgen EX-70, manufactured by TAKEMOTO OIL & FAT CO., LTD.): 50 parts by weight
(2) Corn oil: 50 parts by weight The above components were mixed at 180° C. for 30 minutes and then left to cool to obtain a blend [C].

[3]
(1) Blend [B]: 50 parts by weight
(2) Blend [C]: 50 parts by weight

The above components were mixed at 80° C. for 5 minutes and then left to cool to obtain a gel formulation.

Example 16

(1) Nicosulfuron (purity: 93.4%): 7.38 parts by weight
(2) A mixture of polyoxyethylene hydrogenated castor oil and dioctyl sulfosuccinate: 10.46 parts by weight
(3) Urea: 3.14 parts by weight
(4) Corn oil: 52.87 parts by weight
(5) EMANON CH-25 (tradename): 26.15 parts by weight The above components were mixed and wet-pulverized for 10 minutes by a wet-grinding machine, to obtain an oil-based suspension concentrate.

Example 17

(1) Nicosulfuron (purity: 93.4%): 7.38 parts by weight
(2) A mixture of polyoxyethylene hydrogenated castor oil and dioctyl sulfosuccinate: 10.46 parts by weight
(3) Urea: 3.14 parts by weight
(4) Corn oil: 47.64 parts by weight
(5) EMANON CH-25 (tradename): 31.38 parts by weight The above components were mixed and wet-pulverized for 10 minutes by a wet-grinding machine, to obtain an oil-based suspension concentrate.

Example 18

(1) Nicosulfuron (purity: 93.4%): 8.56 parts by weight
(2) Geropon T/36 (tradename): 3 parts by weight
(3) Supragil WP (tradename): 2 parts by weight
(4) Condensate of sodium alkylnaphthalenesulfonate with formalin (tradename: Supragil MNS/25, Rhodia Nicca, Ltd.): 5 parts by weight
(5) Clay (tradename: MS clay, manufactured by Fubasami-clay Co., Ltd.): 9.44 parts by weight
(6) EMANON CH-25 (tradename): 40 parts by weight
(7) Carplex #80 (tradename): 32 parts by weight Molten EMANON CH-25 was adsorbed on Carplex #80, and then other components were mixed thereto to obtain a wettable powder.

Example 19

(1) Nicosulfuron (purity: 93.4%): 8.56 parts by weight
(2) Geropon T/36 (tradename): 3 parts by weight
(3) Supragil WP (tradename): 2 parts by weight
(4) Supragil MNS/25 (tradename): 5 parts by weight
(5) MS Clay (tradename): 9.44 parts by weight
(6) EMANON CH-80 (tradename): 40 parts by weight
(7) Carplex #80 (tradename): 32 parts by weight Molten EMANON CH-25 was adsorbed on Carplex #80, and then other components were mixed thereto to obtain a wettable powder.

Test Example 1

Upland field soil was filled in a 1/1,000,000 ha pot, seeds of crabgrass (*Digitaria sanguinalis* L.) were sown therein and grown in a green house. When crabgrass reached 3 leaf stage, a prescribed amount (20 g a.i./ha) of water-dispersible granules containing nicosulfuron as an active ingredient, formulated in accordance with Example 1, was diluted with water corresponding to 300 liters/ha, and an alkoxylated glyceride was added thereto in a concentration of 0.05 wt %, followed by foliar application. Further, for the purpose of comparison, foliar application was carried out in the same manner by using an ethoxylated tallow amine type adjuvant (tradename: Frigate, manufactured by ISK Biosciences Europe S.A.) instead of the alkoxylated glyceride.

On the 21st day after the application of the herbicide, the growth of crabgrass was visually observed (growth inhibition rate (%)=0:untreated plot to 100:complete kill), whereby the results as shown in Table 1 were obtained.

The following is evident from Table 1. Frigate as a commercially available adjuvant enhanced the herbicidal effect of nicosulfuron. Whereas, the alkoxylated glyceride enhanced the herbicidal effect of nicosulfuron more distinctly even at the same concentration.

TABLE 1

|  | Alkoxylated glyceride (tradename) | Growth inhibition rate (%) |
| --- | --- | --- |
| Present invention | EMANON CH-25 | 75 |
|  | EMANON CH-80 | 74 |
|  | EMALEX GWIS-340 | 86 |
|  | EMALEX GWIS-360 | 80 |
|  | EMALEX GWIS-115 | 57 |
|  | EMALEX GWIS-125 | 64 |
|  | PYROTER GPI-25 | 59 |
|  | PYROTER CPI-60 | 76 |
| Comparison | Frigate | 37 |
|  | Nil | 3 |

Test Example 2

Upland field soil was filled in a 1/1,000,000 ha pot, and seeds of black nightshade (*Solanum nigrum* L.) were sown therein and grown in a green house. When black nightshade reached 2.2 leaf stage, a prescribed amount (20 g a.i./ha) of water-dispersible granules containing nicosulfuron as an active ingredient, formulated in accordance with Example 1, was diluted with water corresponding to 300 liters/ha, and an alkoxylated glyceride was added thereto in a concentration of 0.1 wt %, followed by foliar application. Further, for the purpose of comparison, foliar application was carried out in the same manner by using a polyoxyethylene sorbitan monolaurate type adjuvant (corresponding to commercially available adjuvant Tween 20, manufactured by NACALAI TESQUE) instead of the alkoxylated glyceride.

On the 21st day after the application of the herbicide, the growth of black nightshade was observed in the same manner as the above Test Example 1, whereby the results as shown in Table 2 were obtained.

The following is evident from Table 2. The polyoxyethylene sorbitan monolaurate as a commercially available adjuvant enhanced the herbicidal effect of nicosulfuron. Whereas, the alkoxylated glyceride enhanced the herbicidal effect of nicosulfuron more distinctly even at the same concentration.

TABLE 2

|  | Alkoxylated glyceride (tradename) | Growth inhibition rate (%) |
| --- | --- | --- |
| Present invention | EMANON CH-25 | 57 |
|  | EMANON CH-80 | 83 |
|  | EMALEX GWIS-340 | 69 |
|  | EMALEX GWIS-360 | 81 |
|  | EMALEX GWIS-115 | 42 |
|  | EMALEX GWIS-125 | 60 |
|  | PYROTER GPI-25 | 53 |
|  | PYROTER CPI-60 | 72 |
| Comparison | Polyoxyethylene sorbitan monolaurate | 48 |
|  | Nil | 0 |

Test Example 3

Upland field soil was filled in a 1/1,000,000 ha pot, and seeds of redroot pigweed (*Amaranthus retroflexus* L.) were sown therein and grown in a green house. When redroot pigweed reached 3.6 leaf stage, a prescribed amount (5 g a.i./ha) of water-dispersible granules containing nicosulfuron as an active ingredient, formulated in accordance with the above Example 1, was diluted with water corresponding to 300 liters/ha, and an alkoxylated glyceride was added thereto in a concentration of 0.025 wt %, followed by foliar application. Further, for the purpose of comparison, foliar application was carried out in the same manner by using an alkylaryl polyglycol ether type adjuvant (tradename: Citowett, manufactured by BASF France) instead of the alkoxylated glyceride.

On the 21st day after the application of the herbicide, the growth of redroot pigweed was observed in the same manner as in Test Example 1, whereby the results as shown in Table 3 were obtained.

The following is evident from Table 3. Citowett as a commercially available adjuvant enhanced the herbicidal effect of nicosulfuron. Whereas, the alkoxylated glyceride enhanced the herbicidal effect of nicosulfuron more distinctly even at the same concentration.

TABLE 3

|  | Alkoxylated glyceride (tradename) | Growth inhibition rate (%) |
| --- | --- | --- |
| Present invention | EMANON CH-25 | 81 |
|  | EMANON CH-80 | 84 |
|  | EMALEX GWIS-340 | 86 |
|  | EMALEX GWIS-360 | 84 |
|  | EMALEX GWIS-115 | 85 |
|  | EMALEX GWIS-125 | 85 |
|  | PYROTER GPI-25 | 81 |
|  | PYROTER CPI-60 | 86 |
| Comparison | Citowett | 76 |
|  | Nil | 66 |

Test Example 4

Upland field soil was filled in a 1/1,000,000 ha pot, and seeds of crabgrass were sown therein and grown in a green house. When crabgrass reached 3 leaf stage, a prescribed amount (15 g a.i./ha) of water-dispersible granules containing flazasulfuron as an active ingredient (tradename: KATANA, manufactured by Ishihara Sangyo Kaisha, Ltd.), was diluted with water corresponding to 300 liters/ha, and an alkoxylated glyceride was added thereto in a concentration of 0.025 wt %, followed by foliar application. Further, for the purpose of comparison, foliar application was carried out in the same manner by using Citowett (the same as in Test Example 3) instead of the alkoxylated glyceride.

On the 21st day after the application of the herbicide, the growth of crabgrass was observed in the same manner as in the above Test Example 1, whereby the results as shown in Table 4 were obtained.

The following is evident from Table 4. Citowett as a commercially available adjuvant enhanced the herbicidal effect of flazasulfuron. Whereas, the alkoxylated glyceride enhanced the herbicidal effect of flazasulfuron more distinctly even at the same concentration.

TABLE 4

| | Alkoxylated glyceride (tradename) | Growth inhibition rate (%) |
|---|---|---|
| Present invention | EMANON CH-80 | 89 |
| | EMALEX GWIS-360 | 84 |
| Comparison | Citowett | 68 |
| | Nil | 43 |

Test Example 5

Upland field soil was filled in a 1/1,000,000 ha pot, and seeds of crabgrass were sown therein and grown in a green house. When crabgrass reached 3 leaf stage, a prescribed amount (15 g a.i./ha) of water-dispersible granules containing trifluoxysulfuron as an active ingredient (tradename: Envoke, manufactured by Syngenta), was diluted with water corresponding to 300 liters/ha, and an alkoxylated glyceride was added thereto in a concentration of 0.025 wt %, followed by foliar application. Further, for the purpose of comparison, foliar application was carried out in the same manner by using Citowett (the same as in Test Example 3) instead of the alkoxylated glyceride.

On the 21st day after the application of the herbicide, the growth of crabgrass was observed in the same manner as in the above Test Example 1, whereby the results as shown in Table 5 were obtained.

The following is evident from Table 5. Citowett as a commercially available adjuvant enhanced the herbicidal effect of trifloxysulfuron. Whereas, the alkoxylated glyceride enhanced the herbicidal effect of trifloxysulfuron more distinctly even at the same concentration.

TABLE 5

| | Alkoxylated glyceride (tradename) | Growth inhibition rate (%) |
|---|---|---|
| Present invention | EMANON CH-80 | 89 |
| | EMALEX GWIS-360 | 90 |
| Comparison | Citowett | 82 |
| | Nil | 52 |

Test Example 6

Upland field soil was filled in a 1/1,000,000 ha pot, and seeds of crabgrass were sown therein and grown in a green house. When crabgrass reached 3 leaf stage, a prescribed amount (20 g a.i./ha) of a wettable powder containing foramsulfuron as an active ingredient, formulated in accordance with the above Example 2, was diluted with water corresponding to 300 liters/ha, and the alkoxylated glyceride was added thereto in a concentration of 0.05 wt %, followed by foliar application. Further, for the purpose of comparison, foliar application was carried out in the same manner by using Citowett (the same as in Test Example 3) instead of the alkoxylated glyceride.

On the 21st day after the application of the herbicide, the growth of crabgrass was observed in the same manner as in the above Test Example 1, whereby the results as shown in Table 6 were obtained.

The following is evident from Table 6. Citowett as a commercially available adjuvant enhanced the herbicidal effect of foramsulfuron. Whereas, the alkoxylated glyceride enhanced the herbicidal effect of foramsulfuron more distinctly even at the same concentration.

TABLE 6

| | Alkoxylated glyceride (tradename) | Growth inhibition rate (%) |
|---|---|---|
| Present invention | EMANON CH-80 | 70 |
| | EMALEX GWIS-360 | 53 |
| Comparison | Citowett | 19 |
| | Nil | 3 |

Test Example 7

Upland field soil was filled in a 1/1,000,000 ha pot, and seeds of velvetleaf (*Abutilon theophrasti* MEDIC.) were sown therein and grown in a green house.

When velvetleaf reached 3 leaf stage, a prescribed amount (20 g a.i./ha) of a wettable powder containing tritosulfuron as an active ingredient, formulated in accordance with the above Example 3, was diluted with water corresponding to 300 liters/ha, and an alkoxylated glyceride was added thereto in a concentration of 0.05 wt %, followed by foliar application.

On the 21st day after the application of the herbicide, the growth of velvetleaf was observed in the same manner as in the above Test Example 1, whereby the results as shown in Table 7 were obtained.

The following is evident from Table 7. The alkoxylated glyceride enhanced the herbicidal effect of the tritosulfuron distinctly in the same manner as in the preceding Test Examples.

TABLE 7

| | Alkoxylated glyceride (tradename) | Growth inhibition rate (%) |
|---|---|---|
| Present invention | EMANON CH-80 | 74 |
| | EMALEX GWIS-360 | 66 |
| Comparison | Nil | 50 |

Test Example 8

Upland field soil was filled in a 1/1,000,000 ha pot, and seeds of crabgrass were sown therein and grown in a green house. When crabgrass reached 3 leaf stage, a prescribed amount (5 g a.i./ha) of a water-dispersible granules containing rimsulfuron as an active ingredient (tradename: TITUS, manufactured by Du Pont) was diluted with water corresponding to 300 liters/ha, and an alkoxylated glyceride was added thereto in a concentration of 0.05 wt %, followed by foliar application. Further, for the purpose of comparison, foliar application was carried out in the same manner by using Citowett (the same as in Test Example 3) instead of the alkoxylated glyceride.

On the 21st day after the application of the herbicide, the growth of crabgrass was observed in the same manner as in the above Test Example 1, whereby the results as shown in Table 8 were obtained.

The following is evident from Table 8. Citowett as a commercially available adjuvant enhanced the herbicidal effect of rimsulfuron. Whereas, the alkoxylated glyceride enhanced the herbicidal effect of rimsulfuron more distinctly even at the same concentration.

TABLE 8

|  | Alkoxylated glyceride (tradename) | Growth inhibition rate (%) |
| --- | --- | --- |
| Present invention | EMANON CH-80 | 80 |
|  | EMALEX GWIS-360 | 81 |
| Comparison | Citowett | 66 |
|  | Nil | 17 |

Test Example 9

Upland field soil was filled in a 1/1,000,000 ha pot, and seeds of crabgrass were sown therein and grown in a green house. When crabgrass reached 3.3 leaf stage, a prescribed amount (35 g a.i./ha) of water-dispersible granules containing nicosulfuron as an active ingredient, formulated in accordance with the above Example 1, was diluted with water corresponding to 300 liters/ha, and an alkoxylated glyceride was added thereto in a concentration of 0.01 wt %, followed by foliar application. Further, for the purpose of comparison, foliar application was carried out in the same manner by using Frigate (the same as in Test Example 1) instead of the alkoxylated glyceride.

On the 22nd day after the application of the herbicide, the growth of crabgrass was observed in the same manner as in the above Test Example 1, whereby the results as shown in Table 9 were obtained.

The following is evident from Table 9. Frigate as a commercially available adjuvant enhanced the herbicidal effect of nicosulfuron. Whereas, the alkoxylated glyceride enhanced the herbicidal effect of nicosulfuron more distinctly even at the same concentration.

TABLE 9

|  | Alkoxylated glyceride (tradename) | Growth inhibition rate (%) |
| --- | --- | --- |
| Present invention | EMANON CH-25 | 78 |
|  | EMANON CH-80 | 78 |
|  | EMALEX GWIS-360 | 82 |
|  | EMALEX TPIS-350 | 66 |
| Comparison | Frigate | 35 |
|  | Nil | 23 |

Test Example 10

Upland field soil was filled in a 1/1,000,000 ha pot, and seeds of crabgrass were sown therein and grown in a green house. When crabgrass reached 3.3 leaf stage, a prescribed amount (30 g a.i./ha) of water-dispersible granules containing nicosulfuron as an active ingredient, formulated in accordance with the above Example 1, was diluted with water corresponding to 300 liters/ha, and an alkoxylated glyceride was added thereto in a concentration of 0.01 wt %, followed by foliar application. Further, for the purpose of comparison, foliar application was carried out in the same manner by using Citowett (the same as in Test Example 3) instead of the alkoxylated glyceride.

On the 22nd day after the application of the herbicide, the growth of crabgrass was observed in the same manner as in the above Test Example 1, whereby the results as shown in Table 10 were obtained.

The following is evident from Table 10. Citowett as a commercially available adjuvant did not enhance the herbicidal effect of nicosulfuron. Whereas, the alkoxylated glyceride enhanced the herbicidal effect of nicosulfuron distinctly even at the same concentration.

TABLE 10

|  | Alkoxylated glyceride (tradename) | Growth inhibition rate (%) |
| --- | --- | --- |
| Present invention | EMANON CH-25 | 75 |
|  | EMANON CH-80 | 79 |
|  | EMALEX GWIS-360 | 79 |
|  | EMALEX TPIS-350 | 59 |
| Comparison | Citowett | 25 |
|  | Nil | 25 |

Test Example 11

Upland field soil was filled in a 1/1,000,000 ha pot, and seeds of crabgrass were sown therein and grown in a green house. When crabgrass reached 3.3 leaf stage, a prescribed amount (30 g a.i./ha) of water-dispersible granules containing nicosulfuron as an active ingredient, formulated in accordance with the above Example 1, was diluted with water corresponding to 300 liters/ha, and an alkoxylated glyceride was added thereto in a concentration of 0.02 wt %, followed by foliar application. Further, for the purpose of comparison, foliar application was carried out in the same manner by using Citowett (the same as in Test Example 3) instead of the alkoxylated glyceride.

On the 22nd day after the application of the herbicide, the growth of crabgrass was observed in the same manner as in the above Test Example 1, whereby the results as shown in Table 11 were obtained.

The following is evident from Table 11. Citowett as a commercially available adjuvant did not enhance the herbicidal effect of nicosulfuron. Whereas, the alkoxylated glyceride enhanced the herbicidal effect of nicosulfuron distinctly even at the same concentration.

TABLE 11

|  | Alkoxylated glyceride (tradename) | Growth inhibition rate (%) |
| --- | --- | --- |
| Present invention | EMANON CH-25 | 89 |
|  | EMANON CH-80 | 87 |
|  | EMALEX GWIS-360 | 88 |
|  | EMALEX TPIS-350 | 84 |
| Comparison | Citowett | 25 |
|  | Nil | 25 |

Test Example 12

Upland field soil was filled in a 1/1,000,000 ha pot, and seeds of barnyard grass (*Echinochloa crus-galli* L.) were sown therein and grown in a green house. When barnyard grass reached 2 leaf stage, a prescribed amount (1.5 g a.i./ha) of water-dispersible granules containing nicosulfuron as an active ingredient, formulated in accordance with the above Example 1, was diluted with water corresponding to 300 liters/ha, and an alkoxylated glyceride was added thereto in a concentration of 0.3 wt %, followed by foliar application. Further, for the purpose of comparison, foliar application was carried out in the same manner by using Citowett (the same as in Test Example 3) instead of the alkoxylated glyceride.

On the 22nd day after the application of the herbicide, the growth of barnyard grass was observed in the same manner as in the above Test Example 1, whereby the results as shown in Table 12 were obtained.

The following is evident from Table 12. Citowett as a commercially available adjuvant enhanced the herbicidal effect of nicosulfuron. Whereas, the alkoxylated glyceride enhanced the herbicidal effect of nicosulfuron more distinctly even at the same concentration.

TABLE 12

|  | Alkoxylated glyceride (tradename) | Growth inhibition rate (%) |
|---|---|---|
| Present invention | EMANON CH-25 | 94 |
|  | EMANON CH-80 | 89 |
|  | EMALEX GWIS-360 | 96 |
|  | EMALEX TPIS-350 | 98 |
| Comparison | Citowett | 56 |
|  | Nil | 30 |

Test Example 13

Upland field soil was filled in a 1/1,000,000 ha pot, and seeds of barnyard grass were sown therein and grown in a green house. When barnyard grass reached 2 leaf stage, a prescribed amount (1.5 g a.i./ha) of water-dispersible granules containing nicosulfuron as an active ingredient, formulated in accordance with the above Example 1, was diluted with water corresponding to 300 liters/ha, and an alkoxylated glyceride was added thereto in a concentration of 0.2 wt %, followed by foliar application. Further, for the purpose of comparison, foliar application was carried out in the same manner by using Citowett (the same as in Test Example 3) instead of the alkoxylated glyceride.

On the 22nd day after the application of the herbicide, the growth of barnyard grass was observed in the same manner as in the above Test Example 1, whereby the results as shown in Table 13 were obtained.

The following is evident from Table 13. Citowett as a commercially available adjuvant enhanced the herbicidal effect of nicosulfuron. Whereas, the alkoxylated glyceride enhanced the herbicidal effect of nicosulfuron more distinctly even at the same concentration.

TABLE 13

|  | Alkoxylated glyceride (tradename) | Growth inhibition rate (%) |
|---|---|---|
| Present invention | EMANON CH-25 | 93 |
|  | EMANON CH-80 | 86 |
|  | EMALEX GWIS-360 | 96 |
|  | EMALEX TPIS-350 | 98 |
| Comparison | Citowett | 35 |
|  | Nil | 30 |

Test Example 14

Upland field soil was filled in a 1/1,000,000 ha pot, and seeds of barnyard grass were sown therein and grown in a green house. When barnyard grass reached 2 leaf stage, a prescribed amount (1.5 g a.i./ha) of water-dispersible granules containing nicosulfuron as an active ingredient, formulated in accordance with the above Example 1, was diluted with water corresponding to 300 liters/ha, and an alkoxylated glyceride was added thereto in a concentration of 0.1 wt %, followed by foliar application. Further, for the purpose of comparison, foliar application was carried out in the same manner by using Frigate (the same as in Test Example 1) instead of the alkoxylated glyceride.

On the 22nd day after the application of the herbicide, the growth of barnyard grass was observed in the same manner as in the above Test Example 1, whereby the results as shown in Table 14 were obtained.

The following is evident from Table 14. Frigate as a commercially available adjuvant enhanced the herbicidal effect of nicosulfuron. Whereas, the alkoxylated glyceride enhanced the herbicidal effect of nicosulfuron more distinctly even at the same concentration.

TABLE 14

|  | Alkoxylated glyceride (tradename) | Growth inhibition rate (%) |
|---|---|---|
| Present invention | EMANON CH-25 | 91 |
|  | EMANON CH-80 | 93 |
|  | EMALEX GWIS-360 | 95 |
|  | EMALEX TPIS-350 | 95 |
| Comparison | Frigate | 53 |
|  | Nil | 30 |

Test Example 15

Upland field soil was filled in a 1/1,000,000 ha pot, and seeds of barnyard grass were sown therein and grown in a green house. When barnyard grass reached 2 leaf stage, a prescribed amount (3 g a.i./ha) of water-dispersible granules containing nicosulfuron as an active ingredient, formulated in accordance with the above Example 1, was diluted with water corresponding to 300 liters/ha, and an alkoxylated glyceride was added thereto in a concentration of 0.1 wt %, followed by foliar application. Further, for the purpose of comparison, foliar application was carried out in the same manner by using Citowett (the same as in Test Example 3) instead of the alkoxylated glyceride.

On the 22nd day after the application of the herbicide, the growth of barnyard grass was observed in the same manner as in the above Test Example 1, whereby the results as shown in Table 15 were obtained.

The following is evident from Table 15. Citowett as a commercially available adjuvant enhanced the herbicidal effect of nicosulfuron. Whereas, the alkoxylated glyceride enhanced the herbicidal effect of nicosulfuron more distinctly even at the same concentration.

TABLE 15

|  | Alkoxylated glyceride (tradename) | Growth inhibition rate (%) |
|---|---|---|
| Present invention | EMANON CH-25 | 94 |
|  | EMANON CH-80 | 99 |
|  | EMALEX GWIS-360 | 97 |
|  | EMALEX TPIS-350 | 97 |
| Comparison | Citowett | 42 |
|  | Nil | 28 |

Test Example 16

Upland field soil was filled in a 1/1,000,000 ha pot, and seeds of crabgrass were sown therein and grown in a green house. When crabgrass reached 3 leaf stage, a prescribed amount (18 g a.i./ha) of water-dispersible granules containing nicosulfuron as an active ingredient, formulated in accordance with the above Example 1, was diluted with water corresponding to 300 liters/ha, and an alkoxylated glyceride and a chelating agent (citric acid or ethylene diamine tetraacetic acid (EDTA)) as a coadjuvant were added thereto in prescribed concentrations, followed by foliar application.

On the 22nd day after the application of the herbicide, the growth of crabgrass was observed in the same manner as in the above Test Example 1, whereby the results as shown in Table 16 were obtained.

The following is evident from Table 16. The alkoxylated glyceride enhanced the herbicidal effect of nicosulfuron. However, when the coadjuvant was further added, the herbicidal effect of nicosulfuron was enhanced more distinctly in spite of the fact that the total amount of the alkoxylated glyceride and the coadjuvant was the same as the amount of the alkoxylated glyceride added alone.

TABLE 16

| Alkoxylated glyceride (tradename) | Chelating agent | Concentration in diluted liquid (wt %) Alkoxylated glyceride | Chelating agent | Growth inhibition rate (%) |
|---|---|---|---|---|
| EMANON CH-80 | — | 0.02 | — | 75 |
| | — | 0.025 | — | 82 |
| | Citric acid | 0.015 | 0.005 | 75 |
| | Citric acid | 0.02 | 0.005 | 93 |
| | EDTA | 0.015 | 0.005 | 80 |
| | EDTA | 0.02 | 0.005 | 94 |

Test Example 17

Upland field soil was filled in a 1/1,000,000 ha pot, and seeds of crabgrass were sown therein and grown in a green house. When crabgrass reached 3 leaf stage, a prescribed amount (20 g a.i./ha) of water-dispersible granules containing nicosulfuron as an active ingredient, formulated in accordance with the above Example 1, was diluted with water corresponding to 300 liters/ha, and an alkoxylated glyceride was added thereto in a concentration of 0.025 wt %, followed by foliar application. Further, for the purpose of comparison, foliar application was carried out in the same manner by using Citowett (the same as in Test Example 3) instead of the alkoxylated glyceride.

On the 21st day after the application of the herbicide, the growth of crabgrass was observed in the same manner as in the above Test Example 1, whereby the results as shown in Table 17 were obtained.

The following is evident from Table 17. Citowett as a commercially available adjuvant enhanced the herbicidal effect of nicosulfuron. Whereas, the alkoxylated glyceride enhanced the herbicidal effect of nicosulfuron more distinctly even at the same concentration.

TABLE 17

| | Alkoxylated glyceride (tradename) | Growth inhibition rate (%) |
|---|---|---|
| Present invention | NIKKOL HCO-5 | 85 |
| | Sorpol HC-10 | 89 |
| | Sorpol HC-20 | 91 |
| | PEGNOL HC-30 | 92 |

TABLE 17-continued

| | Alkoxylated glyceride (tradename) | Growth inhibition rate (%) |
|---|---|---|
| | Sorpol HC-40 | 94 |
| | Sorpol HC-50 | 93 |
| | Sorpol HC-80 | 94 |
| | Sorpol HC-100 | 93 |
| | Sorpol HC-150 | 93 |
| Comparison | Citowett | 8 |
| | Nil | 2 |

Test Example 18

Upland field soil was filled in a 1/1,000,000 ha pot, and seeds of crabgrass were sown therein and grown in a green house. When crabgrass reached 3 leaf stage, a prescribed amount (15 g a.i./ha) of the one obtained by the formulation method in the above Example 17, was diluted with water corresponding to 300 liters/ha, followed by foliar application. Further, for the purpose of comparison, foliar application was carried out in the same manner using a prescribed amount (15 g a.i./ha) of Onehope NYUZAI (manufactured by ISK BIOSCIENCES K.K.) as a commercial product containing nicosulfuron as an active ingredient.

On the 21st day after the application of the herbicide, the growth of crabgrass was observed in the same manner as in the above Test Example 1, whereby the results as shown in Table 18 were obtained.

The following is evident from Table 18. The oil-based suspension concentrate of the present invention containing the alkoxylated glyceride exhibited a distinctive herbicidal effect, even at a dose (15 g a.i./ha) lower than the standard dose of Onehope NYUZAI.

TABLE 18

| | Formulation | Growth inhibition rate (%) |
|---|---|---|
| Present invention | Example 17 | 72 |
| Comparison | Onehope NYUZAI | 48 |

Test Example 19

Upland field soil was filled in a 1/1,000,000 ha pot, and seeds of crabgrass were sown therein and grown in a green house. When crabgrass reached 3 leaf stage, a prescribed amount (20 g a.i./ha) of water-dispersible granules containing nicosulfuron as an active ingredient, formulated in accordance with the above Example 1, was diluted with water corresponding to 300 liters/ha, and an alkoxylated glyceride and a nitrogen-containing fertilizer (tradename: ANBLA, manufactured by Sankyo Co., Ltd., ammoniacal nitrogen: water-soluble phosphoric acid:water-soluble potassium=4:30:16) were added thereto at prescribed concentrations, followed by foliar application.

On the 21st day after the application of the herbicide, the growth of crabgrass was observed in the same manner as in the above Test Example 1, whereby the results as shown in Table 19 were obtained.

The following is evident from Table 19. The alkoxylated glyceride enhanced the herbicidal effect of nicosulfuron. However, when the nitrogen-containing fertilizer was added, the herbicidal effect of nicosulfuron was further enhanced.

TABLE 19

| Alkoxylated glyceride (tradename) | Nitrogen-containing fertilizer (tradename) | Concentration in diluted liquid (wt %) | | Growth inhibition rate (%) |
|---|---|---|---|---|
| | | Alkoxylated glyceride | Nitrogen-containing fertilizer | |
| EMANON CH-80 | — | 0.025 | — | 90 |
| | ANBLA | 0.025 | 0.005 | 93 |

The invention claimed is:

1. A herbicidal composition comprising a herbicidal sulfonylurea compound or its salt, and a polyoxyethylene glyceride,
   wherein the herbicidal sulfonylurea compound or its salt is at least one herbicidal sulfonylurea compound selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flucetosulfuron, flupyrsulfuron, foramsulfuron, halosulfuron-methyl, imazosulfuron, iodosulfuron, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, and tritosulfuron, or salts thereof; and
   wherein said polyoxyethylene glyceride is not polyoxyethylene hydrogenated castor oil.

2. The herbicidal composition according to claim 1, wherein the polyoxyethylene glyceride is at least one selected from the group consisting of, polyoxyethylene glyceryl monostearate, polyoxyethylene glyceryl triisostearate, polyoxyethylene glyceryl monoisostearate, polyoxyethylene glyceryl tristearate, polyoxyethylene glyceryl distearate, polyoxyethylene glyceryl trioleate, polyoxyethylene hydrogenated castor oil monoisostearate, polyoxyethylene hydrogenated castor oil triisostearate, polyoxyethylene hydrogenated castor oil monolaurate, polyoxyethylene 1,1,1-trimethylolpropane tristearate, polyoxyethylene 1,1,1-trimethylolpropane trimyristate, polyoxyethylene 1,1,1-trimethylolpropane distearate, polyoxyethylene 1,1,1-trimethylolpropane triisostearate, polyoxyethylene hydrogenated castor oil pyroglutamic acid isostearate, and polyoxyethylene glyceryl pyroglutamic acid isostearate.

3. The herbicidal composition according to claim 1, wherein the polyoxyethylene glyceride is at least one selected from the group consisting of polyoxyethylene glyceryl triisostearate, polyoxyethylene glyceryl monoisostearate, polyoxyethylene 1,1,1-trimethylolpropane triisostearate, polyoxyethylene hydrogenated castor oil pyroglutamic acid isostearate, and polyoxyethylene glyceryl pyroglutamic acid isostearate.

4. The herbicidal composition according to claim 1, wherein the herbicidal sulfonylurea compound or its salt is at least one herbicidal sulfonylurea compound selected from the group consisting of flazasulfuron, foramsulfuron, nicosulfuron, rimsulfuron, trifloxysulfuron, and tritosulfuron, or salts thereof.

5. The composition of claim 1, which does not contain nicosulfuron.

6. The herbicidal composition of claim 1 comprising:
   a herbicidal sulfonylurea compound or its salt selected from the group consisting of nicosulfuron, flazasulfuron, trifuloxysulfuron, foramsulfuron, tritosulfuron, and rimsulfuron; and
   an alkoxylated glyceride,
   wherein when said herbicidal sulfonylurea is nicosulfuron, said herbicidal composition does not contain polyoxyethylene hydrogenated castor oil.

7. The herbicidal composition according to claim 6, wherein the alkoxylated glyceride is at least one alkoxylated glyceride selected from the group consisting of polyoxyethylene glyceryl triisostearate, polyoxyethylene glyceryl monoisostearate, polyoxyethylene 1,1,1-trimethylolpropane triisostearate, polyoxyethylene hydrogenated castor oil pyroglutamic acid isostearate, and polyoxyethylene glyceryl pyroglutamic acid isostearate.

8. The herbicidal composition according to claim 1, which comprises the herbicidal sulfonylurea compound or its salt, and the polyoxyethylene glyceride in a weight ratio of from 16:1 to 1:6000.

9. A method for controlling at least one undesired plant or for inhibiting the growth of the at least one undesired plant, comprising applying the herbicidal composition as defined in claim 8 to the at least one undesired plant or to a place where the at least one undesired plant grows.

10. The herbicidal composition according to claim 1, which comprises from 0.1 to 95 parts by weight of the herbicidal sulfonylurea compound or its salt, from 0.1 to 94.9 parts by weight of the polyoxyethylene glyceride, and the rest being additives for formulation.

11. A method for controlling at least one undesired plant or inhibiting the growth of the at least one undesired plant, comprising applying the herbicidal composition as defined in claim 10 to a place where the at least one undesired plant grows.

12. The herbicidal composition according to claim 1, which further comprises one or more other herbicidal compounds.

13. The herbicidal composition according to claim 1, which further comprises a coadjuvant.

14. The herbicidal composition according to claim 1, which further comprises one or more other herbicidal compounds and a coadjuvant.

15. The herbicidal composition according to claim 13, wherein the coadjuvant is a chelating agent, fertilizer comprising nitrogen, or a combination thereof.

16. A method for controlling at least one undesired plant or for inhibiting the growth of the at least one undesired plant, comprising contacting at least one undesired plant or a place where the undesired plant grows with the herbicidal composition as defined in claim 1.

17. The method of claim 16, wherein said herbicidal composition further comprises a coadjuvant.

18. The method of claim 16, wherein said herbicidal composition further comprises a coadjuvant and one or more other herbicidal compounds.

19. The method of claim 16 that comprises applying 10 to 3,000 liters of said herbicidal composition diluted in water per hectare,
   wherein the amount of the polyoxyethylene glyceride in the diluted herbicidal composition ranges from 0.005% to 4%; and
   wherein the blend ratio of the sulfonylurea compound or its salt and the polyoxyethylene glyceride ranges from 16:1 to 1:6,000.

20. The method of claim 16, wherein said herbicidal composition further comprises one or more other herbicidal compounds.

* * * * *